（12）United States Patent
Martucci

(10) Patent No.: US 7,141,251 B2
(45) Date of Patent: Nov. 28, 2006

(54) PHARMACOLOGICALLY ACTIVE STRONG ACID SOLUTIONS

(75) Inventor: David Martucci, San Francisco (VE)

(73) Assignee: Cytorex Biosciences, inc., Coral Springs, FL (US)

( * ) Notice: Subject to any disclaimer, the term of this patent is extended or adjusted under 35 U.S.C. 154(b) by 325 days.

(21) Appl. No.: 10/114,537

(22) Filed: Apr. 2, 2002

(65) Prior Publication Data

US 2003/0035847 A1 Feb. 20, 2003

Related U.S. Application Data

(60) Provisional application No. 60/282,026, filed on Apr. 6, 2001.

(51) Int. Cl.
*A61K 33/42* (2006.01)
*A61K 31/19* (2006.01)
*A61K 33/04* (2006.01)
*A61K 33/16* (2006.01)
*A61K 33/20* (2006.01)

(52) U.S. Cl. ................. 424/605; 424/666; 424/673; 424/703; 514/574

(58) Field of Classification Search ............... 424/605, 424/666, 673, 703; 514/574
See application file for complete search history.

(56) References Cited

U.S. PATENT DOCUMENTS

| 4,281,654 A | 8/1981 | Shell et al. |
| 4,675,120 A | 6/1987 | Martucci |
| 5,504,102 A | 4/1996 | Agharkar et al. |
| 5,512,200 A | 4/1996 | Garcia |
| 5,552,389 A | 9/1996 | Toge et al. |
| 5,733,888 A | 3/1998 | Carver et al. |
| 5,977,164 A | 11/1999 | Carver et al. |

OTHER PUBLICATIONS

Mariarosaria Santillo, et al., "Inhibitors of Ras Farnesylation Revert the Increased Resistance of Oxidative Stressin K-ras Transformed NIH 3T3 Cells", Biochemical and Biophysical Research Communications, vol. 229, pp. 739-745, Oct. 23, 1996.
Salvador Harguindey, et al., "Effects of Systemic Acidification of Mice with Sarcoms 180", Cancer Research, vol. 39, pp. 4364-4371, Nov., 1979.
Koing Bo Kwun, et al., "Treatment of Metabolic Alkalosis With Intravenous Infusion of Concentrated Hydrochloric Acid", The American Journal of Surgery, vol. 146, pp. 328-330, Sep., 1983.

*Primary Examiner*—S. Mark Clardy
*Assistant Examiner*—Frank Choi
(74) *Attorney, Agent, or Firm*—Lott & Friedland , PA

(57) ABSTRACT

A composition and therapeutic methods therefore for pharmacologically strong acid solutions comprising a mixture of strong and weak acids.

70 Claims, 5 Drawing Sheets
(1 of 5 Drawing Sheet(s) Filed in Color)

PHARMACOLOGICALLY ACTIVE STRONG ACID SOLUTIONS

CLAIM OF PRIORITY

This application is related to provisional application Ser. No. 60/282,026 filed on Apr. 6, 2001 based upon which priority is claimed pursuant to 35 U.S.C. §119(e).

TECHNICAL FIELD

The present invention relates to compositions and methods of use of a pharmacologically active acid solution in general and more particularly concerns the use of a low pH mixture of strong and weak acids wherein the availability of hydronium ions in the mixture is highly controllable and which is non-corrosive to metals and innocuous to skin or other organic materials and is capable of topical or internal administration.

BACKGROUND OF THE INVENTION

The present invention relates to compositions of strong acid solutions and therapeutic methods therefore.

More particularly, the invention relates to the use of a composition comprising a mixture of strong and weak acids, the final composition acting as a buffer and having a pH of 1 or below.

Scientists are engaged in a constant battle to identify new therapeutics for treatment and prevention of disease in animals in general, and specifically in humans. The search for active agents which are useful against cancer is particularly acute. At present, a number of drugs are approved for treatment of cancer. Recent approvals include Taxol® (paclitaxel), Cisplatin®, Taxotere® (docetaxel). None of these products are active against all forms of cancer, all of them have significant side effects due to their cytotoxic effect on otherwise healthy cells. Due to the extreme toxicity of most cancer therapeutics, treating the cancer with such agents requires that the attending physician walk a fine line between treating the cancer and killing the patient. Patients experience severe discomfort and a noted reduction in quality of life due to side effects of chemotherapy such as alopecia, general disruption of the digestive system and feelings of malaise and general lack of well being. Despite the power of modem cytotoxic agents, many cancers such as glioblastoma are treated with only limited success using currently accepted medical practices. As such, there is a long felt need for additional cancer therapeutics. There is a particular need for therapeutics that offer efficacy, low side effects and generally improve a patient's quality of life.

Acids have been used in pharmaceutical chemistry for decades, primarily in the creation of acid addition salts of bases having therapeutic application. Lists of pharmacologically acceptable acids for the creation of such salts are well known and are exemplified throughout the patent literature. See U.S. Pat. No. 4,281,654 for a typical example.

The use of strong acids alone or in combination as a therapeutic is relatively unknown to the scientific community. However, there are a number of uses of acids as stabilizing agents. U.S. Pat. Nos. 5,733,888 and 5,977,164, entitled *Injectable Composition* and *Stabilized Pharmaceutical Composition*, issued to David Carver, et al., describe and claim the use of various acids for stabilizing a pharmaceutical formulation. Similarly, U.S. Pat. No. 5,504,102 also discloses the use of acids to stabilize a pharmaceutical composition.

The use of acid compositions alone is relatively unknown in the literature. U.S. Pat. No. 5,552,389 describes and claims a method of using Phosphoric acid diesters to treat liver cancer. Santillo, M., et al., *Inhibitors of Ras Farnesylation Revert the Increased Resistance to Oxidative Stress in K-Ras Transformed NIH 3T3 Cells,* 229(3) Biochem. Biophys. Res. Commun. 739–45 (December 1996) discloses that phosphonic acid may suppress certain tumor genes. Kwun, K. B., et al., *Treatment of Metabolic Alkalosis with Intravenous Infusion of Concentrated Hydrochloric Acid,* 146(3) Am J Surg 328–30 (September 1983) discloses the intravenous infusion of hydrochloric acid. Harguindey, S, et al., *Effects of Systemic Acidification of Mice with Sarcoma 180,* 39(11) Cancer Res 4364–71 (November 1979) discloses that mineral acidification of food decreased tumor growth and increased the rate of tumor regression.

Strong acid solutions having unique properties are disclosed in U.S. Pat. No. 4,675,120, issued to David J. Martucci, which describes and claims an acid composition comprising water, hydrochloric acid, phosphoric acid, oxalic acid, citric acid and hydrofluoric acid useful for crude oil recovery.

Topical cosmetic or disinfectant uses of a strong acid composition similar to that disclosed in U.S. Pat. No. 4,675,120 are disclosed in U.S. Pat. No. 5,512,200, which describes and claims a four acid core composition having very low pH comprised of a first and second inorganic acid and third and fourth organic acids. Inorganic acids disclosed include sulfuric, hydrochloric, hydrofluoric and phosphoric. Organic acids disclosed include oxalic and citric acids. The first and second acids are present in a concentration between 5 and 20%. The third and fourth inorganic acids are present in an amount between 1 and 5% of the final composition. The above composition is said to be useful when applied topically as an antibacterial or antifungal agent.

To date there has been no apparent development of strong acid solutions for pharmaceutical use. Particularly, there has been no effort to explore the potential internal uses for these unique agents.

SUMMARY OF THE INVENTION

In accordance with the present invention, herein disclosed is a pharmaceutical composition comprising a mixture of four strong acids and two weak acids effective in treating a variety of medical conditions.

Numerous other advantages and features of the present invention will become readily apparent from the following description of the preferred embodiments of the invention, the accompanying examples, and the appended claims.

BRIEF DESCRIPTION OF THE DRAWINGS

The patent or application file contains at least one frawing executed in color. Copies of this patent with color drawing(s) will be provided by the Patent and Trademark Office upon request and payment of the necessary fee.

DETAILED DESCRIPTION OF THE INVENTION

Figure 1:
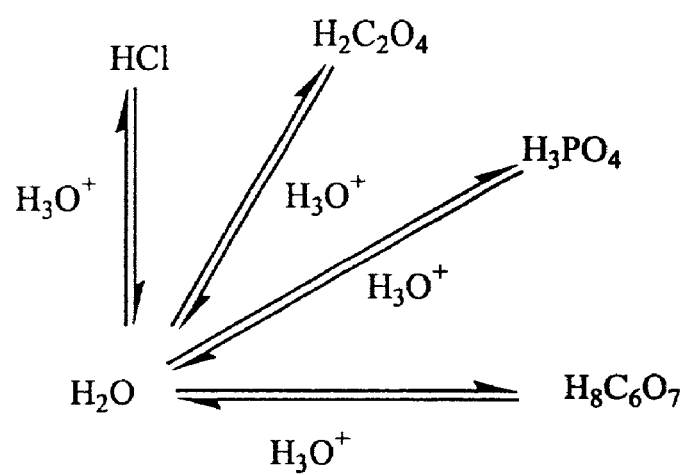
FIG. 1 shows the relationships between the hydronium ion donors and acceptors in the strong acid formulations of the present invention.

The present invention discloses and teaches a new acid buffer solution and its uses as a pharmacologically active agent. By following the teachings of the present invention, it is possible to create a buffered system comprising an equilibrium mixture of strong acids conjugated with relatively weaker acids. The system is obtained by respectively combining the strong acid with another strong acid and two relatively weaker acids in the presence of water such that the conjugate bases of the relatively weaker acids serve as strong bases for controlling the hydronium ion availability or production from the strong acids. In this manner, the characteristics of the strongest of the two strong acids can be regulated.

It is therefore an object of the present invention to provide a pharmacologically active buffered acid solution which exhibits low pH levels coupled with highly controllable hydronium ion availability.

It is another object of the present invention to provide a low pH mixture of acids, which mixture is non-corrosive to metals used in the medical field to administer medication for example but not limited intravenous needles and is innocuous to skin or other organic materials.

It is still another object of the present invention to provide a mixture of two strong/weak acid pairs wherein the dissociation of the relatively weaker acid in each acid pair supplies a conjugate base capable of functioning as a strong base relative to the strong acid in each pair, thereby furnishing a means to control the hydronium ion availability or production from the strong acid.

It is yet another object of the invention to utilize the buffered strong acid compositions taught here in for the treatment or prevention of disease.

Another object of the present invention is to provide a pharmacological agent suitable for internal or external use.

It is a further object of the invention to treat cellular abnormalities such as cancer.

It is a further object of the present invention to reduce side effects normally associated with cancer therapeutics by administering the buffered strong acid solutions of the present invention.

It is yet another object of the invention to increase the life of catheters and other access methods to the circulatory system.

A. Formation of the Strong Acid Solutions

In a preferred embodiment of the present invention, a buffered solution is made in two parts. A base strong acid solution is made from two strong and two weak acids. Additional strong acids are added to the base strong acid solution to create the buffered strong acid solution.

To create the base solution two strong and two weak acids are mixed to establish a mechanism for controlling hydronium ion availability in the acids. A first balancing system is maintained between the conjugates of one of the strong acids and the conjugates of a relatively weaker acid. The remaining pair of acids likewise forms a balancing system consisting of relatively strong and relatively weak acid conjugates. For present purposes, hydrochloric acid (HCl) and oxalic acid ($H_2C_2O_4$) are chosen as the strong acids while phosphoric acid ($H_3PO_4$) and citric acid ($H_8C_6O_7$) are chosen as the weak acids relative to the strong acids.

From a comparative point of view, the application of Bronsted-Lowry theory to the acid ionization reactions of hydrochloric, oxalic, phosphoric and citric acids will yield the following relationships between the conjugates of each acid:

TABLE 1

| Acid | Grade of Ionization ($\alpha$) | Acid Conjugate Relationship |
|---|---|---|
| HCl | $\alpha = 1$ | Strong acid/weak conjugate base |
| $H_3PO_4$ | $\alpha < 1$ | Weak acid/strong conjugate base |
| $H_2C_2O_4$ | $\alpha = 1$ | Strong acid/weak conjugate base |
| $H_8C_6O_7$ | $\alpha < 1$ | Weak acid/strong conjugate base |

The relationship expressed in Table 1 can better be understood by observing the actual ionization reactions of each acid within the context of the two strong/weak acid systems. Mixing the hydrochloric and phosphoric acids creates the first system of strong/weak acid pairs. In a water environment, hydrochloric acid dissociates according to the following equation:

$$HCl + H_2O \rightarrow Cl^- + H_3O^+ \qquad \text{Eq.1}$$

Similarly, in a water environment, phosphoric acid is dissociated into three ionization states of decreasing strength as respectively characterized by Equations 2–4:

$$H_3PO_4 + H_2O \Longleftrightarrow H_2PO_4^- + H_3O^+ \qquad \text{Eq.2}$$

$$H_2PO_4^- + H_2O \Longleftrightarrow HPO_4^{-2} + H_3O^+ \qquad \text{Eq.3}$$

$$HPO_4^{-2} + H_2O \Longleftrightarrow PO_4^{-3} + H_3O^+ \qquad \text{Eq.4}$$

The main source of hydronium ions in the mixture of hydrochloric and phosphoric acids is provided by the dissociation of the hydrochloric acid. Theoretically, it can be seen that the chlorine ions ($Cl^-$) also produced as a result of the ionization expressed in Equation 1 provide a salt for the hydrochloric acid. Given the strength of the hydrochloric acid, however, the chlorine ions as a practical matter cannot reassociate with hydronium ions at a rate fast enough to maintain a state of equilibrium during ionization. Hence, the production of hydronium ions in pure hydrochloric acid remains unregulated. In contrast, when phosphoric acid is added to the hydrochloric acid, the ionization of phosphoric acid will serve as a partial regulator or controller of the hydronium availability in the hydrochloric/phosphoric acid mixture. Such regulation occurs because the first ionization state of phosphoric acid, i.e., $H_2PO_4^-$, is present in relatively great concentration within the mixture of hydrochloric and phosphoric acids. While considered a semi-weak base per se, the first ionization state of phosphoric acid acts as a relatively strong base in the presence of the strong hydrochloric acid. Consequently, the first ionization constant of phosphoric acid plays a primary role in capturing free hydronium ions present in the mixture of hydrochloric and phosphoric acids.

Despite the modifying effect of phosphoric acid on hydrochloric acid, the level of hydronium ion availability in a mixture of hydrochloric and phosphoric acids is too high to provide effective control over the mixture. A second pair of strong and weak acids, e.g., oxalic and citric acids, must therefore be introduced to the mixture before actual control can be achieved. To this end, oxalic and citric acids are added to the hydrochloric/phosphoric mixture to provide a second strong/weak acid pair. The dissociation reactions of oxalic and citric acids are again analyzed in a water environment, respectively yielding the following equations:

$$H_2C_2O_4 + H_2O \Longleftrightarrow HC_2O_4^- + H_3O^+ \qquad \text{Eq. 5}$$

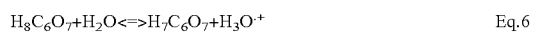

$$H_8C_6O_7 + H_2O \Longleftrightarrow H_7C_6O_7^- + H_3O^+ \qquad \text{Eq. 6}$$

Although the hydrochloric acid serves as the primary source of hydronium ions in the two strong/weak pairs of acids, the oxalic acid is a relatively strong acid in its own right and thus constitutes a secondary source of hydronium ions when added to the mixture of hydrochloric and phosphoric acids. The availability of the additional hydronium ions from the oxalic acid is quite important inasmuch as these additional hydronium ions are responsible for the low pH of the full solution, i.e., the solution of hydrochloric, phosphoric, oxalic and citric acids.

The action of the citric acid in the full solution is also important. Adding oxalic acid alone to the hydrochloric and phosphoric acid mixture would produce an over-abundance of hydronium ions, destroying the sought-after control of hydronium ion availability. The citric acid, however, is considered a weak acid, particularly in relation to the oxalic acid. As a result, the ionization state of the citric acid serves as a strong conjugate base for the oxalic acid. This strong conjugate base in turn provides a secondary mechanism for controlling the availability of hydronium ions from both the primary and secondary hydronium ion sources, i.e., from both the hydrochloric and oxalic acids, in the full solution.

The entire mechanism for achieving control over hydronium ion availability in the mixture of the present invention can now be understood. The first ionization state of phosphoric acid created by combining the first strong/weak or hydrochloric/phosphoric acid pair and the ionization state of citric acid created by combining the second strong/weak or oxalic/citric acid pair act in concert as relatively strong bases to regulate the production of free hydronium ions within the solution. The first ionization state of phosphoric acid and the ionization state of citric acid are both decreased by respectively drawing off free hydronium ions, thereby causing an increase in the concentration of phosphoric acid and citric acid in the solution. This latter condition favors the ionization state of the hydrochloric and oxalic acids, in the process providing a strong source of hydronium ions and allowing the ionization reactions expressed in Equations 2 and 6 to reach a state of equilibrium. The ionization of the oxalic acid additionally produces oxalate ions which act as a strong base relative to the hydrochloric acid, providing another means for capturing hydronium ions. As a net result, overall control of hydronium ion availability in the full solution is readily attainable notwithstanding the very low pH of the solution.

It should be noted in connection with the ionization reactions discussed above that water plays a key role in the actual ionizing and dissociation mechanisms of the various acids in the present invention. Equations 1, 2, 5 and 6 all demonstrate that water functions as a strong "base" during the dissociation reactions, furnishing a carrier for the hydrogen ions released by the acids of the present invention. In this manner, the various ionizations are greatly facilitated while the exchange of hydronium ions necessary to maintain equilibrium between the various dissociations and reassociations, and hence control over hydronium ion availability, is achieved. The key role of water in the present invention, and in particular the role of water in transporting hydronium ions between the reactants of Equations 1, 2, 5 and 6, is amply illustrated in FIG. 1.

The above acid solutions provide a stable environment that appears to regulate the otherwise corrosive effect of hydrofluoric acid (HF) and sulfuric acid ($H_2SO_4$) on tissues.

It has been discovered that new formulations of strong acids can be formulated for pharmaceutical use. A person of skill in the art will recognize that the formulations described herein can be constructed of a wide range of acids and concentrations by weight or volume. For example, the hydrochloric acid can range from 3–25 percent by weight, the oxalic acid from 0.1–10 percent by weight w/w, the phosphoric acid from 3–10 percent by weight and the hydrofluoric acid from 1–30 percent by weight. Preferred is a composition in which the hydrochloric acid ranges from 5–15 percent by weight, the oxalic acid ranges from 0.15–2 percent by weight, the phosphoric acid ranges from 2–7 percent by weight and the hydrofluoric acid ranges from 2–7 percent by weight. Most preferred is a formulation containing hydrochloric acid at 12 percent by weight, oxalic acid at 0.3 percent by weight, phosphoric acid at 6 percent by weight, sulfuric acid at 16 percent by weight and hydrofluoric acid at 5 percent by weight.

Formulation 1

First making a base solution from two strong and two weak acids to which further strong and weak acids are added can manufacture a buffered strong acid solution suitable for internal use. Table 2 lists the relative concentrations of hydrochloric acid, phosphoric acid, oxalic acid, citric acid and water in the base solution used to make one preferred embodiment of the present invention.

TABLE 2

| Component | % Concentration by Weight |
|---|---|
| Oxalic Acid ($H_2C_2O_4$) | 2% |
| Citric Acid ($H_8C_6O_7$) | 2% |
| Hydrochloric Acid (HCl, d = 1.15 g/cc) | 6% |
| Phosphoric Acid ($H_3PO_4$, d = 1.70 g/cc) | 6% |
| Water ($H_2O$) | 84% |

In order to create 1000 ml of the base solution (Base Solution 1) from which the buffer is created, the components listed in Table 2 are combined in the following sequence:

(a) Oxalic acid (20 grams), which is generally in solid form, is added to 200 ml water in a suitable reaction vessel at ambient temperature and is completely solubilized under continuous agitation;

(b) Following solubilization of the oxalic acid, citric acid (20 grams), which is generally in solid form, is added to the oxalic acid solution obtained in (a) at ambient temperature with an additional 200 ml of water and is completely solubilized under continuous agitation;

(c) Following solubilization of the citric acid, the HCl (60 grams) is then added to the solution of (b) while maintaining continuous agitation.

(d) Phosphoric acid (60 grams) is added to the solution obtained in (c) while maintaining continuous agitation.

(e) The resulting mixture obtained in (d) is agitated until all components are dissolved. Water is added slowly until a final volume of 1000 ml is obtained.

Adding the component of Table 3 to the Base Solution 1 creates the buffered strong acid solution:

TABLE 3

| Component | Density g/ml |
| --- | --- |
| Base Solution 1 | N/A |
| Sulfuric Acid ($H_2SO_4$) | 1.84 |
| Hydrochloric Acid (HCl) | 1.15 |
| Phosphoric Acid ($H_3PO_4$) | 1.70 |
| Hydrofluoric Acid (HF) | 1.10 |

Using the following steps creates 1000 ml of buffered strong acid.
  (a) Add 150 ml of Base Solution 1 to a clean glass container.
  (b) Slowly add 100 ml of sulfuric acid in small quantities, not to exceed 10 ml, with continuous stirring. This is a highly exothermic reaction which generates a very significant amount of heat. Allow the sulfuric acid/Base Solution 1 mixture to cool to ambient laboratory temperature.
  (c) To the cool mixture from step (b), slowly add 30 ml phosphoric acid with continuous stirring.
  (d) To the cool mixture from step (c), slowly add 100 ml hydrochloric acid with continuous agitation.
  (e) Change the reaction vessel and stirring apparatus from glass to plastic.
  (f) To the mixture from Step (d), add 50 ml hydrofluoric acid with continuous stirring.
  (g) Add sufficient additional water to complete an aggregate amount of 1000 ml of the buffered strong acid solution.

The buffered strong acid solution prepared according to the foregoing sequence of steps is characteristically modified in the sense that the solution has a pH of less than 1, has strong buffering capacity and is completely stable at ambient temperatures between 0 and 70° C. and normal light. The buffered strong acid solution is non-corrosive and non-toxic, e.g., innocuous to skin. It is surprising that the HF contained in the buffered strong acid solution of present invention does not burn the skin. The exact manner by which the solution avoids damage to the skin has not yet been determined.

Although exhibiting the beneficial characteristics discussed above, the solution of Formulation 1 maintains a high level of acidizing potential. That is, the pH level of the solution is quite low, generally on the order of less than 1.

Formulation 2

Altering the concentrations of the acids can create an alternative embodiment of a strong acid solution having medical use, but very limited buffering capacity. Similar to Formulation 1, Formulation 2 is created from a base of the four acids set forth in Table 4, which lists the relative concentrations of hydrochloric acid, phosphoric acid, oxalic acid, citric acid and water in Base Solution.

TABLE 4

| Component | % Concentration By Weight |
| --- | --- |
| Oxalic Acid ($H_2C_2O_4$) | 3% |
| Citric Acid ($H_8C_6O_7$) | 3% |
| Hydrochloric Acid (HCL, d = 1.15 g/cc) | 5% |
| Phosphoric Acid ($H_3PO_4$, d = 1.70 g/cc) | 5% |
| Water ($H_2O$) | 84% |

In order to create 1000 ml of the base solution (Base Solution 2) from which Formulation 2 is created, the components listed in Table 4 are combined in the following sequence:
  (a) Oxalic acid, which is generally in solid form, is added to 200 ml water in a suitable reaction vessel at ambient temperature and is completely solubilized under continuous agitation;
  (b) Following solubilization of the oxalic acid, citric acid, which is generally in solid form, is added to the oxalic acid solution of (a) at ambient temperature and is completely solubilized under continuous agitation;
  (c) Following solubilization of the citric acid, the hydrochloric is added to the solution obtained in step (b), while maintaining continuous agitation.
  (d) Phosphoric acid is added to the solution obtained in step (c), while maintaining continuous agitation.
  (e) Sufficient water is added to the solution obtained in step (d), complete an aggregate amount of 1000 ml of this low pH solution (Base Solution 2).
  (f) The resulting mixture obtained in step (e) is agitated until all components are fully dissolved.

The topical strong acid solution (Formulation 2) is created by mixing the components of Table 5

TABLE 5

| Component | % Concentration By Volume |
| --- | --- |
| Base Solution 2 | 40 |
| Sulfuric Acid ($H_2SO_4$, d = 1.84 g/cc) | 20 |
| Hydrochloric Acid (HCl, d = 1.15 g/cc) | 10 |
| Phosphoric Acid ($H_3PO_4$, d = 1.70 g/cc) | 10 |
| Hydrofluoric (HF, d = 1.10 g/cc) | 15 |
| Glycerin (d = 1/24 g/cc) | 5 |

1000 ml of topical strong acid is created by using the following steps:
  (a) Add 400 ml of Base Solution 2 to a clean glass container.
  (b) Slowly add 200 ml of sulfuric acid to the Base Solution 2 with continuous stirring. This is a highly exothermic reaction which generates a very significant amount of heat. Allow the sulfuric acid/base Solution 2 mixture to cool to ambient laboratory temperature.
  (c) To the cool mixture obtained in step (b), slowly add 100 ml phosphoric acid with continuous stirring.
  (d) To the mixture obtained in step (c), slowly add 100 ml of HCl with continuous agitation.
  (e) Change the reaction vessel and stirring apparatus from glass to plastic.

(f) To the mixture obtained in step (d), slowly add 150 ml HF with continuous stirring.

(g) To the mixture from step (f), add 50 ml of glycerin.

The strong acid solution prepared according to the foregoing sequence of steps is characteristically modified in the sense that the solution has a very low pH, and is completely stable at ambient temperatures between 0 and 70° C. and normal light. The strong acid solution is non-corrosive and non-toxic, e.g., innocuous to skin. It is surprising that the HF contained in the strong acid solution of Formulation 2 does not burn the skin. The exact manner by which the solution avoids damage to the skin has not yet been determined.

B. Pharmaceutical Uses and Administration of Strong Acid Solutions

The buffered strong acid solution (Formulation 1) may be administered in any medically accepted manner, except that solid dosages forms may be difficult to produce due to the pH. These compounds of the present invention are administered in a pharmaceutical composition and may include suitable excipients, the composition being useful in treating disease. Method of formulating compositions for an intended pharmaceutical use are well known in the art. A generally recognized compendium of such methods and ingredients is *Remington's Pharmaceutical Sciences* by E. W. Martin (Mark Publ. Co., 15 Ed., 1975), which is hereby incorporated by reference herein.

Methods of administration include but are not limited to: topical, oral, intravenous (IV), intramuscularly, intraperitoneal, rectal, intra-urethral, intravesical, and intravaginal. The most preferred methods for Formulation 1 are oral or IV, either peripheral or subclavian/central. Formulation 2 can only be administered topically and internal administration of Formulation 2 may be lethal.

When administering the buffered strong acid solution orally, patients may be given between 5 and 1000 drops of Formulation 1 per day. The buffered strong acid solution Formulation 1 can be administered directly to a patient, however, the preferred patient dosage is from 10–200 drops per day diluted in 100–1000 ml. of liquid, preferably juices prepared from fresh fruit, not from concentrate. Most preferred is 20–30 drops in 200 ml of liquid. Citrus juices or other acid containing beverages should be avoided due to increased potential for irritation of the digestive tract and possible reaction with the buffered strong acids of this invention. Milk and dairy based beverages should be avoided because the acids will curdle the milk.

In a preferred form of administration, patients are initially titrated from a dose of 20–30 drops in 200 cc of Formulation 1, diluted in non-citrus fruit juices, given for 1–2 days and the patient observed for any adverse reaction. If no reaction is observed, the dose can be escalated to 20 drops 3 times a day and adjusted upward, as tolerated by an individual patient. A suggested daily dose after titration is 100–150 drops per day, however, some patients may not tolerate more than 70 drops per day. It is preferred that the daily dosage be divided into 20–30 drop quantities and administered at appropriately spaced intervals throughout the day. Formulation 1 should generally be added to a minimum of 200 ml of liquid, 20 drops are equivalent to 1 cc or 1 ml of fluid.

It is important that this product not be taken on an empty stomach. While there are generally no side effects from ingesting the buffered acid composition as described above, the added acids may cause heartburn and/or acid indigestion. At the discretion of the attending physician, precautions should be taken when giving this product orally to patients who have a history of digestive tract problems or who are undergoing chemotherapy. Recommended precautions comprise a premedication regimen comprising $H_2$ blockers, digestive tract anti-inflammatories and/or an anti-emetic. The premedication regimen should be administered one half to one hour before administration of Formulation 1 in accordance with the product labeling each agent administered.

Due to the difficulties of administration and the apparent bioavailablity of the buffered strong acids of Formulation 1 when administered orally, IV administration is less preferred except when the patient requires higher doses than may be tolerable through oral administration. In such instances, the buffered strong acid solutions taught herein can be administered through any suitable vein. Most preferred for the highest doses and for frequent dosing is administration through a surgically implanted subclavial catheter. When administering the buffered strong acid solution IV, it should be diluted in a suitable IV fluid such as glucose, dextrose or saline. In such instances 8 ml of buffered strong acid may be diluted in 250–1000 ml of infusion fluids. It is preferred to administer 2 ml of the Formulation 1 in approximately 250 ml of infusion fluids. The preferred rate of infusion is 20–40 drops per minute at which rate it will take approximately 4–8 hours to administer the solution. Higher dosages are also possible, for example, 100 drops administered in 500 ml of fluid. However, with higher concentrations, the infusion rate should be reduced to approximately 25 drops per minute.

When administering buffered strong acid solutions IV, peripherally, such as through a vein in the arm or leg, it is preferable to use a very fine and long needle and dose the patient every other day or one week e.g., Monday, Wednesday and Friday, followed by a one week rest and then resume an every other day infusion schedule. Because there appears to be no dose limiting toxicity when administered as described herein, there is no limit on how long a patient may be dosed with the buffered strong acid solutions of Formulation 1. If reactions occur in the veins, topical application of an anti-inflammatory may help.

It should be readily apparent to one of skill in the art that combinations of routes of administration such as but not limited to oral and IV administration (either peripheral or sub-clavian) are possible and may be desirable when seeking to administer higher or more frequent doses to a patient.

Intra-muscular administration is possible but may be less preferred because of the formation of lesions. Similarly, intra-peritoneal administration is also possible, but may not be desirable due to the need to administer in a hospital setting.

The formulations disclosed in this patent are generally safe for administration when used as directed herein. However, certain patients will require extra care prior to administration of the pharmaceutical formulations disclosed in this patent. For example, in patients with high blood levels of creatinine and urea which may be indicative of kidney failure, it is advisable to bring these values within normal range prior to treatment with the formulations disclosed herein. Similarly, it is also desirable to correct conditions of low blood pressure, below 90/60, prior to treatment with the internal formulations disclosed in this application.

Formulation 1 does not affect blood pH when administered in accordance with the methods described in this patent. It is generally known that when an acid is added to extra-cellular fluid, it is rapidly absorbed by the carbonic acid/bicarbonate buffer which is the primary regulator of $H_3O^+$ levels in living systems. The buffered acid formulations disclosed herein contain closely regulated levels of $H_3O^+$. As such the buffering systems in living beings appears to be able to absorb any additional amounts introduced through the buffered strong acids. The hydrofluoric acid, which is the primary free acid in the formulation, contributes little $H_3O^+$. It is postulated but unproven that hydrofluoric acid may form important complexes with proteins or other buffering agents leading to the surprising activity of buffered acid solutions. The mechanism of action of the present formulation is a matter for further research and investigation.

At present, the formulations disclosed in this application when administered as described herein have shown unique activity against a number of medical conditions.

It has been discovered that subclavial ports can be left in for extended periods of time. Normally, such ports last 7–10 days before their use be replaced, due to infection. Patient's administered the formulations disclosed herein have shown no sign of infection around the port for periods as long as 95 days. It is believed that this effect is due to the activity of Formula 1 against most known bacterial, viral and fungal infections.

Antiviral activity has been demonstrated in vitro and in a clinical setting. Both Formulation 1 and 2 disclosed herein have demonstrated activity in patients against the Human Papilloma Virus (HPV), Polio virus and Encephalitis virus.

Data have shown that the formulations disclosed herein are selective neoplastic agents that appear to have no impact on normal healthy cells. The compositions only attack neoplastic cells. Animal studies demonstrated the destruction of chromatin in neoplastic cells while normal cells remained unaffected. Tumors are affected without affecting normal tissues.

Not only are the strong acid compositions disclosed herein effective in treating known tumors in patients, experiments have shown that the strong acid solutions prevent the formation of tumors. The present invention also appears to prevent or treat micro metastasis.

Very surprising is the observation that the buffered strong acid formulations are effective in treating brain tumors. It is postulated that unlike most chemotherapeutic agents, the active moiety of the buffered strong acid formulation is able to cross the blood brain barrier. This is evidenced by tumor shrinkage and by a reduction of pressure in the cranial cavity.

Administration of Formulations 1 and 2 has shown antimycotic activity against all known fungi.

Cancer patients receiving the buffered strong acid of Formulation 1 disclosed herein are able to stop taking pain medication. For reasons unknown, the strong acid buffered solutions serve to alleviate pain in cancer patients.

The buffered strong acids have shown significant reductions in tumoral markers. As shown in the examples, reductions to normal levels have been observed in TM 15-3 in breast cancer and PSA in prostate and also in alkaline phosphatase levels in patients with bone cancer metastasis.

When administered as described herein, the buffered strong acid formulations have been shown to generally improve the quality of life for cancer patients. They feel stronger in a couple of days after initiating treatment. Significantly, they experience a return of appetite and normal sleeping patterns. Patients immobilized due to exhaustion or pain often regain mobility.

The buffered strong acid solutions also appear to have significant benefit on the circulatory system. A significant lowering of blood pressure has been observed in patients receiving buffered strong acids where prescription medication failed to have effect. The buffered strong acids can be used either alone or in conjunction with prescription medication.

Table 6 lists the acceptable ranges of concentration for each of the acids added to the Formulations 1 and 2.

TABLE 6

| Component | Range (% volume) |
| --- | --- |
| Hydrofluoric Acid | 1–40% |
| Hydrochloric Acid | 2–30% |
| Sulfuric Acid | 2–30% |
| Phosphoric Acid | 1–30% |

The strong acid solutions of Formulation 1 and 2 can be used for the treatment of a wide range of diseases. Formulation 1 is appropriate for internal administration to treat cancer, high blood pressure, infectious disease of viral, bacterial or fungal origin including human Papilloma virus and HIV. Formulation 1 when given intravenously extends the life of catheters and other venous access ports. Formulation 2 is appropriate for topical administration to treat melanoma and infections of the skin. Specific examples showing the use of the strong acid compositions of Formulations 1 and 2 are set forth below.

EXAMPLE 1

Melanoma Cells

Formulation 1 was diluted with saline solution in concentrations of 1.10 to 1:100,000 and plated in petri dishes containing growth media and melanoma cell line murine B-16 from Jackson Hospital mice. Dilutions of 1:10 to 1:100,000 of Formulation 1 were plated. The results are shown in Table 7.

TABLE 7

| Dilution | # Of Surviving Cells |
| --- | --- |
| Control | 100% |
| 1:10 | 0 |
| 1:100 | 0 |
| 1:1,000 | 0 |
| 1:10,000 | 0 |
| 1:100,000 | 0 |

These results show that the Formulation 1 is a powerful cytotoxic agent

EXAMPLE 2

Bacteria

Formulation 1 was tested for anti-bacterial activity using Kirby-Bauer methods. *staphylococcus aureus, Escheria coli, Klebiella pneumoniae, Pseudomonas aerigonosa, Acinebacter Baumannii, Enteroccoccus*, spp. were grown in soy media at 35° C. for 16–18 hours and diluted with saline to 0.5 McFarland and plated on Mueller-Hinkle plates. 0.1 ml of Formulation 1 was added to each plate and dried. Each plate was incubated 18–21 hours at 35° C. All bacteria present were destroyed.

EXAMPLE 3

Encephalitis

The effects of Formulation 1 on encephalitis were tested in kidney derived Green Monkey VERO cells.

Protocol

VERO cells having a normal life span of 7–10 days were grown in Eagle MEM with 10% Bovine Fetal Serum and 1% antibiotic/anti-mycotic mycotic agent in 25 cm3 cultures. Testing for activity of Formulation 1 against encephalitis was performed using the following controls and experimental plates.

Negative Control comprised of a plated monolayer of VERO cells on the maintenance medium containing 2% Bovine Fetal Serum.

Toxicity Control comprised of a plated monolayer of VERO cells on the maintenance medium containing 2% Bovine Fetal Serum with 600 µl of undiluted Formulation 1 added.

Positive Control comprised of a plated monolayer of VERO cells on the maintenance medium containing 2% Bovine Fetal Serum and inoculated with 600 µl Goajira version of encephalitis virus.

Experiment 1 comprised of a plated monolayer of VERO cells on the maintenance medium containing 2% Bovine Fetal Serum and inoculated with 600 µl Goajira version of encephalitis virus with 600 µl of undiluted Formulation 1 added to the plate.

Experiment 2 comprised of a plated monolayer of VERO cells on the maintenance medium containing 2% Bovine Fetal Serum and inoculated with 600 µl Goajira version of encephalitis virus with 600 µl of Formulation 1 diluted 1:2 with water added to the plate.

Experiment 3 comprised of a plated monolayer of VERO cells on the maintenance medium containing 2% Bovine Fetal Serum and inoculated with 600 µl Goajira version of encephalitis virus with 600 µl of Formulation 1 diluted 1:10 with water added to the plate.

All plates were initially incubated for 1 hour at 37° C. in 5% $CO_2$ to allow viral adsorption. Formulation 1 was added to those plates identified above and the cultures were maintained at 37° C. and observed.

Results and observations

Those plates receiving Formulation 1 turned a uniform yellow color as soon as Formulation 1 was added.

On the second day post infection, the cytotoxic effects of the virus was evident in 75% of the monolayer of the positive control. In the negative control, the monolayer remained confluent and demonstrated no morphological changes to the cells. The experimental plates 1, 2 and 3 which contained Formulation 1 also remained confluent and demonstrated no morphological changes to the cells.

On the 5th day post infection, the virus destroyed all the cells in the positive control. The cells of the negative control remained confluent but showed expected signs of aging. The cells of the experimental plates 1, 2 and 3 remained a confluent monolayer and showed no signs of aging.

Two months post infection, the cells of the experimental plates 1, 2 and 3 remained alive and demonstrated no signs of aging.

Three months post infection, the laboratory where the experiments were conducted suffered a long term power outage. All of the ongoing experiments in the laboratory were destroyed except for the experimental plates containing Formulation 1.

EXAMPLE 4

Polio Virus

Formulation 1 was tested against poliovirus in African Monkey derived MA104 cells.

Protocol

MA104 cells having a normal life span of 7–10 days were grown in Eagle MEM with 10% Bovine Fetal Serum and 1% antibiotic/antimycotic agent in 25 cm3 cultures. Testing for activity of Formulation 1 against encephalitis was performed using the following controls and experimental plates.

Negative Control comprised of a plated monolayer of MA104 cells on the maintenance medium containing 2% Bovine Fetal Serum.

Toxicity Control comprised of a plated monolayer of MA104 cells on the maintenance medium containing 2% Bovine Fetal Serum with 600 µl of undiluted Formulation 1 added.

Positive Control comprised of a plated monolayer of MA104 cells on the maintenance medium containing 2% Bovine Fetal Serum and inoculated with 600 µl poliovirus.

Experiment 1 comprised of a plated monolayer of MA104 cells on the maintenance medium containing 2% Bovine Fetal Serum and inoculated with polio virus with 600 µl of undiluted Formulation 1 added to the plate.

Experiment 2 comprised of a plated monolayer of MA104 cells on the maintenance medium containing 2% Bovine Fetal Serum and inoculated with polio virus with 600 µl of Formulation 1 diluted 1:2 with water added to the plate.

Experiment 3 comprised of a plated monolayer of MA104 cells on the maintenance medium containing 2% Bovine Fetal Serum and inoculated with polio virus with 600 µl of Formulation 1 diluted 1:10 with water added to the plate.

All plates were initially incubated for 2 hours at 37° C. in 5% $CO_2$ to allow viral adsorption. Formulation 1 was added to those plates identified above and the cultures were maintained at 37° C. and observed.

Results and observations

Those plates receiving Formulation 1 turned a uniform yellow color as soon as Formulation 1 was added.

On the third day post infection, the cytotoxic effects of the polio virus was evident in 50% of the monolayer of the positive control. In the negative control, the monolayer remained confluent and demonstrated no morphological changes to the cells or signs of aging. The experimental plates 1, 2 and 3 which contained Formulation 1 also remained confluent and demonstrated no morphological changes to the cells or signs of aging.

On the 5th day post infection, the virus destroyed 100% of the cells in the positive control. The cells of the negative control remained confluent but showed expected signs of aging. The cells of the experimental plates 1, 2 and 3 remained a confluent monolayer and showed no signs of aging.

Two months post infection, the cells of the experimental plates 1, 2 and 3 remained alive and demonstrated no signs of aging.

Three months post infection, the laboratory where the experiments were conducted suffered a long term power outage. All of the ongoing experiments in the laboratory were destroyed except for the experimental plates containing Formulation 1.

EXAMPLE 7

Venereal Tumors

A female canine was diagnosed with nodular vaginal tumor. The nodule was a soft homogenous tumor of 1.5 cm in diameter. Formulation 2 was topically applied to the surface of the tumor daily for 7 days. By the $7^{th}$ day, the tumor had shrunk from a round nodule to a 1.5 cm plaque. There was no effect to surrounding residual cells. Tissues were analyzed by microscopy and determined to still be neoplastic. Formulation 2 was determined to have significant anti-tumor activity, even though some neoplastic cells remained. It was noted that Formulation 2 had no effect on healthy tissues.

EXAMPLE 8

Lymphoma

A canine great dane, age 7 years was disguised with cutaneous lymphoma and lymphatic sarcoma. Subject had open and oozing ulcerations on the skin. Subject was treated with 25 cc of Formulation 1 subcutaneously and 3 ml of a 1:10 cc Formulation 1 given intramuscularly. Formulation 1 was administered every other day for one (1) month. During treatment, the ulcerations dried up. Subject died nine (9) days post treatment of causes unrelated to treatment.

EXAMPLE 9

Venereal Tumors

A female Doberman, aged 6 years, was diagnosed with tumors of the vulva and vagina. The vaginal tumor was the size of a small lemon and exhibited persistent bleeding. The tumor was surgically removed and the subject treated with chemotherapy. The tumor returned in 30 days with hemorrhaging. Subject was treated with Formulation 1 topically for two (2) days, during which time the hemorrhaging continued. After two (2) days, 0.25 ml of Formulation 1 was injected into the tumor in conjunction with topical administration. The dosing regimen was repeated every other day for 20 days, upon which time, the tumor disappeared. A parenchymal tumor of the mammary gland of the same subject was injected with 0.25 ml of Formulation 1. This tumor disappeared in 48 hours, leaving an opening in the site, where injected.

In a separate experiment, 3 male, 3 female and 3 fixed canines were diagnosed with venereal tumors. Formulation 2 was applied topically to the tumors once a day for 15 days. Formulation 1 was administered IV 0.5 cc daily in 11.5 cc of fluid suitable for IV administration. Clinically, all bleeding tumors stopped bleeding and a reduction was noted in all tumors. In all instances of IV administration, there was no observable change in the subjects hematology, urinalysis or blood chemistry. However, if not administered directly to a vein, there were signs of edema and localized necrosis. Only one (1) subject had a tumor return within 30 days of cessation of treatment.

EXAMPLE 10

Head and Neck Cancer

A 46 year old male patient diagnosed with a 2 cm carcinoma of the tongue was unsuccessfully treated with chemotherapy and radiation. Patient was diagnosed with a possible cancerous tumor in the tongue and underwent a biopsy which confirmed the tumor was cancerous. Three months later patient underwent surgery to remove the tumor. A biopsy of the removed tissue confirmed that it was cancerous. Following the surgery patient underwent 6 weeks of chemotherapy comprising 5-Fluorouracil, carboplatin, interferon and retinoids. Two weeks following the chemotherapy, the patient received radiation therapy and was treated with Vesanoid® (tretinoin) for five months post radiation. The patient continued to have high tumoral markers, lost weight and felt weak and tired. Patient's tumor markers were Ki67-2+; PCNA-3+; P53-3+. (2 is considered moderate and 3 is considered elevated).

One year post diagnosis, patient start taking twenty (20) drops of Formulation 1 diluted in 250 ml of fruit juice was administered three (3) times per day for 90 days. Tests taken fifteen months post diagnosis showed that the patient's T and B cells were back within normal range but that there was a slightly elevated CD4 count and suppressor cells. The patient's CD4/CD8 ratio was substantially reduced. Patient rapidly regained vitality and today shows no signs of cancer except for an elevated CD4/CD8 count, which the attending physician considers normal for this patient.

EXAMPLE 11

Head and Neck Cancer

Figure 2A:
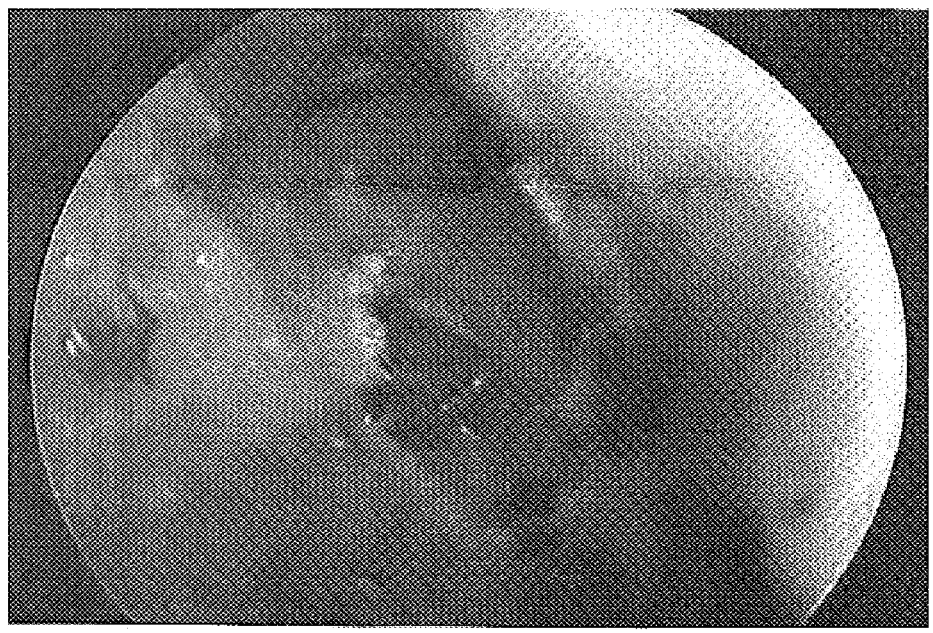
FIG. 2A is a photograph of a patient's ear with a tumor.

A female patient age 5 was diagnosed with a Granulomatoid lesion in the right ear (Hystiocitosis X) following a biopsy. At the time of diagnosis the tumor completely obstructed the ear canal of the right ear and was bleeding. A picture of the tumor is shown in FIG. 2A. Three weeks later the patient initiated oral treatment with Formulation 1 at a dose of 20 drops 3 times a day. When treatment was initiated the patient received an abdominal echogram which identified a bent gallbladder and a slightly enlarged pancreas but with no other abnormalities. The following week a cranial X-ray was taken showing perforations in the cranium. A bone scan performed six weeks post diagnosis identified an abnormal accumulation of the radiotracer in the head, close to the right ear, confirming the original diagnosis. At this time the patient experienced a bloody secretion from her right ear, but was otherwise doing well. the following week, a cytogenetical study is performed for a granuloma eosinofilicus tumor. In 94% of the metaphase cells a normal complement was observed. However, two karyotypes were identified with close complement to the tetraploidia with five copies of the chromosomes 7, 14, 20 and 21; three copies of chromosomes 17, 18 and 19, and four copies of the other autosome chromosomes. Conclusions: There has not been established a clear correlation with the presence of cytogenetic alterations in the patients with granuloma eosinofilicus. However, a karyotype tretraploide hides is the forecast in hematological malignancies.

Figure 2B:
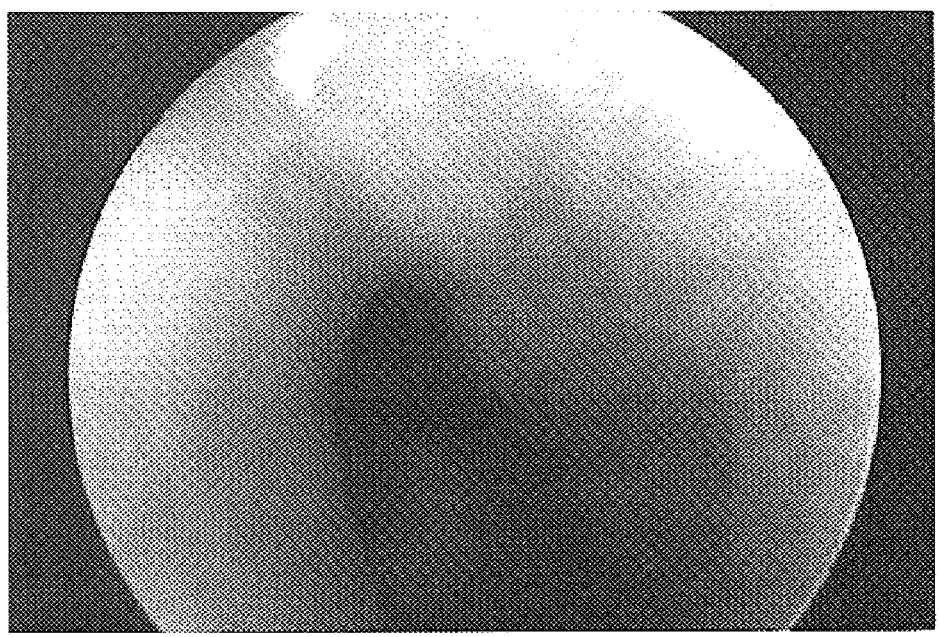
FIG. 2B is a photograph of patient's ear inf FIG. 2A after treatment with Formulation 1 of the present invention.

Four months post diagnosis the patient's mother indicates that her health is improving and that the patient has resumed normal sleep habits and had a good appetite. Urination was normal although patient suffered slight constipation. The secretions from the ear had ceased and any malodors had ceased. Examination by an otolaryngologist shows that the tumor had shrunk to a circle of approximately 2¼ cm diameter, and suggested to continue treatment with Formulation 1. A CAT scan taken at four and a half months post diagnosis does not identify any lesions. At six months post diagnosis the tumor is undetectable. At eight months post diagnosis, the otolaryngologist confirms total disappearance of tumor from the ear. One year post diagnosis, the patient was considered to be in normal health and free of any tumor. FIG. 2B shows the right ear of the patient after treatment with Formulation 1.

EXAMPLE 12

Breast Cancer

A 34 year old female patient diagnosed with breast cancer underwent a mastectomy for the tumor. A biopsy on the tissue confirmed that the tumor was an infiltrating carcinoma of the breast. Four months after the mastectomy, the patient was diagnosed via CAT scan with a neoplastic metastasis from the breast cancer in her hip. This diagnosis was confirmed two months later through an MRI. The tumors were surgically removed and the patient underwent 8 rounds of therapy with Taxol® with concominant treatment with Vesanoid®. At 31 months after diagnosis, and following the Taxol therapy, this patient had high tumor markers. CA 15.3 markers were 71.73 and CA 125 was 40.50. At this time patient began taking 80 drops per day of Formulation 1. Four weeks after starting treatment with Formulation 1, this dose was increased to 120 drops per day. The Ca 15.3 maker and the Alkaline phosphatase (AP) level began to decrease immediately following the increase in dosage. For 10 months, the patient has only been treated with Formulation 1, 120 drops per day. Eleven months after initiating treatment with Formulation 1, all of the patient's tumor markers were normal and the alkaline phosphatase level continued to decrease.

EXAMPLE 13

Breast Cancer

Female patient, aged 78, was diagnosed with a tumor in her left breast. Tumor continued to increase in size over a 2 year period following diagnosis. During that time the patient had lost weight and looked pale. A mammography and biopsy showed a 2.5 cm nodular lesion in the breast with a diagnosis of lobular infiltrating carcinoma. Due to her advanced age, surgical intervention was inadvisable. Patient began taking Formulation 1 orally, 10 drops per day gradually increasing the dose to 50 drops a day for 2 months. Patient had no observable side effects. Two months after initiating oral treatment, patient started IV treatment of 0.5 cc per day of Formulation 1 in glucose every other day for 1 month. Following intravenous administration the patient experienced some phlebitis and edema in her arm. During the month of IV treatment, the patient's skin color improved and she gained 2 kgs. of weight. After one month of IV therapy, the patient resumed oral treatment of Formulation 1 at a dose of 50–60 drops a day for 1 year and 4 months. Another mammography was performed and showed a 4 cm mass but surprisingly showed that the axilar lymphs region was free of malignancy. Today the patient continues oral therapy using Formulation 1 and is alive and in good health.

EXAMPLE 14

Breast Cancer

Female patient, aged 37 under went a biopsy and was diagnosed with Ductal infiltrating Carcinoma in the left breast. 16 region al adenopathies were identified and surgically removed, of which 10 were malignant. The patient was treated by an oncologist with 6 cycles of the following drugs: Farmarubicin, Taxol, Daxorubicin, 5-FU, Citoxan, Ethyol, Cardioxane, Zofran, and Decadron among others. Patient was treated with: 2 cycles of chemotherapy, then 30 sessions of radiotherapy in the affected area and then the remaining 4 cycles of chemotherapy. Following chemotherapy, patient was placed on Evista and Raloxifen. One year after ending chemotherapy, patient suffered nausea, almost permanent headaches and a sensation of pressure in her head and was diagnosed with a brain tumor. At that time patient was depressed and anxious but suffered no memory or language problems or problems with mobility. Patient suffered from paresis in left side of face and in her left limb.

A CAT scan performed at that time shows the existence of a cystic mass 6.5 cm×6.5 cm, with thick capsule in left parietal side compatible with a possible metastatic lesion (melanoma, coriocarcinoma), glioblastoma multiforme or cerebral abscess. With an antecedent of adenocarcinoma is very possible that is that one. MRI ratified the observation made in the CAT. Treating physicians were surprised that with the existence of a large lesion that there was not a big edema.

The patient underwent surgery one month after diagnosis of the brain tumor and, under general anesthesia, a left parietal craniotomy was performed identifying a lesion that was infiltrating the dura mater. The lesion was detached easily. The lesion was of cystic nature and 6 to 8 cc of dark amber color liquid were extracted. The capsule was of varied thickness and was very differentiated from the rest of the cerebral parenquima, with almost no vascularization. The capsule was whitish and granular showing evidence of a malignant tumor. The resection was complete and the dura mater was scraped and cauterized with no macroscopic evidence of the tumor.

A biopsy of the frozen tumor confirmed a diagnosis of metastatic adenocarcinoma in the left parietal side of the brain. Post surgery, patient underwent 10 sessions of radiotherapy of 300 CGY each for a total of 3000 CGY. She was instructed to take Medrol (a corticosteroid) and Neubion (a B complex vitamin) for 2 weeks followed by phenobarbital for 6 months. After 2 months post surgery the patient had not regained her vigor. At that time patient initiated treatment using 30 drops of Formulation 1 orally per day, increasing to 120 drops per day, which is continued to this day. Eight months post surgery, the patient visited an Oncologist at Jackson Memorial Hospital in Miami, who found her to be in very good state of health after performing a set of tests. During a one year period the patient has taken a total of 620 cc of Formulation 1 orally.

EXAMPLE 15

Cancer of the Digestive Tract

A 53 year old male patient was diagnosed with epidermoid carcinoma of big cells in the anal region at which time the patient was hospitalized and treated with 3 cycles of 5FU and Leucovorin and 25 cycles of radiation therapy. The tumor did not respond to therapy and caused problems with urination and defecation. One month post diagnosis the patient was advised his cancer was terminal. Two months post diagnosis, the patient initiated treatment with Formulation 1 at a dose of 140 drops a day (7 cc) and continued treatment for 8 months. At eight months, the dosage was reduced to 100 drops per day, which dose has been maintained until the filing of this application. The patient's hemoglobin value rose from 5 to 11 during the treatment period and the patient regained his appetite and gained weight. All difficulties with urination, defecation an rectal bleeding disappeared. The patient received no other treatment for his cancer during the time he was administered Formulation 1.

EXAMPLE 16

Condylomata Acuminata

Condylomata Acuminata are genital warts caused by certain human papillomaviruses (HPV). A study was performed by a dermatologist on 20 male patients between the age of 20 and 25 years of age. Location of the condilomas was on the penis glade and on the inside of the skin of the penis. Formulation 2 was applied full strength with a Q-tip, allowing the drug to work for the next 24 hours. Afterwards the affected region was washed with soap and water and the regiment repeated every seven days for 3–4 weeks. Following treatment; 5 Cases healed with one application, 8 Cases healed with two applications, and 5 Cases healed with three applications. Two Cases did not return to doctor's appointment after the first treatment.

EXAMPLE 17

Multifocal Basal Cellular Cancer in the Face

Female patient, age 11, was diagnosed following a biopsy with multifocal basal cellular cancer in the face. The tumors were removed surgically on two occasions following, which the tumors immediately returned and spread. Formulation 2 was administered full strength every other day for five applications. The tumors disappeared and have not returned.

EXAMPLE 18

Malignant Melanoma in the Left Leg

Female patient, aged 67, underwent surgery twice to remove melanoma from her left leg. Patient was symptom free for five years when inguinal lymphs in the left leg showed increased in volume. Patient was treated daily with full strength Formulation 2 topically with a cotton swab for a total of six treatments in the affected area. Following treatment, the lymphs reduced volume until they almost disappeared. The patient however died due to recidivisms with metastasis in the pulmonary and liver lymphs.

EXAMPLE 19

Endodermic Papilloma in Left Arm

Patient suffered from Endodermic papilloma in the left arm. Tumor was resistant to all treatment for a period of ten years. Formulation 2 was applied full strength every half hour the same day for two days, followed by administration every other day for two weeks. Following treatment with Formulation 2, the disease has disappeared and has not returned

EXAMPLE 20

Brain Cancer Medulloblastoma

A 27 year old male patient complaining of headaches was diagnosed with a medulloblastoma following a CAT scan and confirmed the following week through an MRI to be a medulloblastoma in the 4th ventricle with hydrocephalia and a possibility of glioma. The patient was only administered analgesics for the headaches. Six months following the initial diagnosis, the tumor had grown to 40×35×32 mm with obstruction of the 4th ventricle. During the 10th month after diagnosis patient was given 3000 CGY of radiation. Eleven months post diagnosis, a drain valve was installed to reduce the pressure and an additional 200 OCGY of radiation administered. Patient continued to suffer from severe headaches, difficulty in walking, nausea, vomiting and blurred vision in his right eye. At approximately one year post diagnosis, an MRI confirms a 3.2×2.7×2.1 tumor. Patient initiated oral treatment with Formulation 1at 30 drops per day increased to 140 drops per day diluted in juice and soups. After one month of treatment the patient began to show significant changes in the pathology of the tumor. The headaches lessened in severity and disappeared within two months of initiation of treatment with Formulation 1. The patient also regained his equilibrium and his vision returned to normal. By the end of the third month of treatment, the patient had resumed all normal daily activities. After approximately four months of treatment with Formulation 1, the patient underwent a CAT scan which indicated "no evidence of apparent intracerebral lesions." This was subsequently confirmed by an MRI.

EXAMPLE 21

Brain Cancer (Glioblastoma Multiforme)

A 38 year old male presented with a convulsive crisis with noticeable weakness in his left arm and leg. CAT scan and MRI confirm a tumor in the right frontal lobe of the brain. Two weeks following diagnosis, the tumor is surgically removed and diagnosed as gemistocystic astrocitoma. A week later the patient was discharged and received radiotherapy over the following three months. Five months after the initial diagnosis, the patient suffered a new convulsive crisis and was readmitted to the hospital. A MRI taken at the time identified an infiltrating lesion affecting the right frontal region and small callous body with small bleeding component and mass effect. Patient was prescribed dilantin, suprabion, pharmaton, aerial, lexotanil, and nonie juice. Patient was also self medicating with Arcalion until ordered to stop by his physician. Approximately one week after the last convulsive crisis, the patient starts oral treatment with Formulation 1 at a rate of 20 drops a day the first day and then increasing the amount to 120 drops a day by the fifth day. Two weeks after the last convulsive crisis the patient was administered 2 cc of Formulation 1 diluted in 500 cc of physiologically acceptable solution, intravenously through the left arm. The administration produced severe itching and was stopped. A second attempt the following week to administer Formulation 1 intravenously was also stopped due to severe itching. Formulation 1 was continued orally at a rate of 120 drops a day. The following week, a subclavian catheter was installed and the patient was administered 2 cc of Formulation 1 in 500 cc of glucose solution three times a day. The catheter was maintained in place for 45 days and the dosing regimen maintained with no signs of infection or signs of reaction to Formulation 1. Following the administration of Formulation 1, the patient was taken off all other medications. His convulsions disappeared and his headaches reduced significantly in frequency and severity. The patient's appetite returned and he was able to sleep. His energy level returned to normal. One year following administration of treatment with Formulation 1, patient continues to take Formulation 1 orally every day and has no clinical manifestations of the tumor. The last MRI taken 9 months after treatment with Formulation 1 shows the tumor to have reduced by 90%. At the filing of this application, the patient continues to take Formulation 1 orally and remains in good health, with no increase in tumor size.

EXAMPLE 22

Ovarian Cancer

Figure 3A:
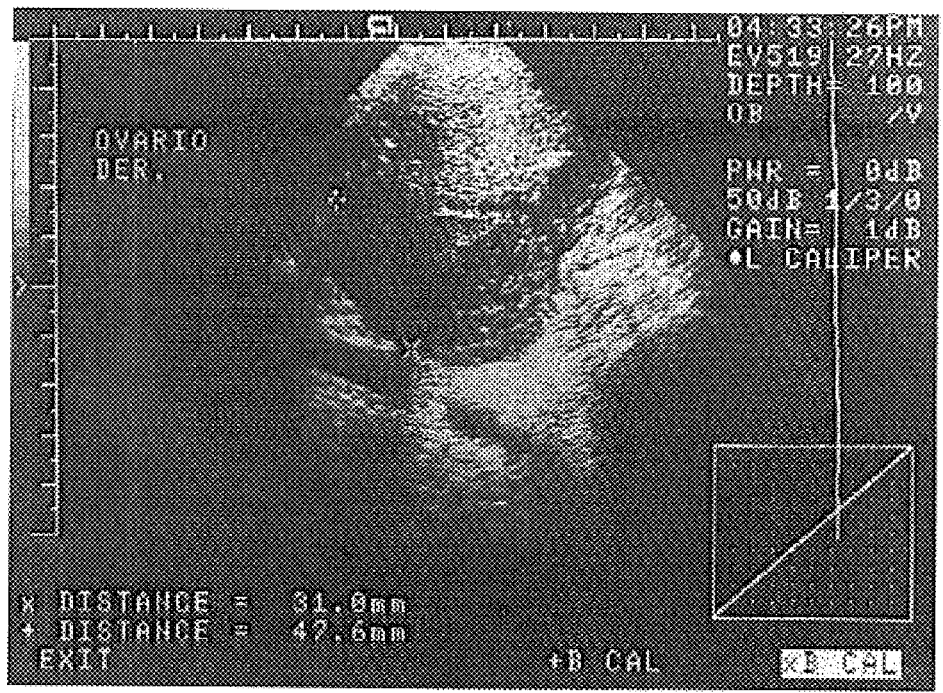
FIG. 3A is an echogram showing an enlarged ovary due to a tumor.
Figure 3B:
FIG. 3B is an echogram showing a normal ovary after the patient of FIG. 3A was treated with Formulation 1 of the present invention.

A female age 37 was diagnosed with terminal ovarian cancer. A CAT scan showed a lesion in the pelvic region of 110×110 mm. Upon undergoing laparotomy, the surgeon identified a mass which spanned from the uterus to the appendix to the rectum. The tumoral mass completely covered the ovary. The surgeon was unable to locate the primary cite of the tumor and did not take a biopsy given the advanced stage of the disease. Patient was given 2 weeks to one month to live. Post surgery, patient was prescribed analgesics for the constant pain. The patient could not eat solid food and was too weak to walk. Chemotherapy and radiotherapy were considered hopeless but nevertheless offered to the patient, who declined to undergo either treatment. Approximately two weeks after surgery, patient initiated oral treatment with Formulation 1 at a dose of 40 drops per day increasing to 120 drops per day over the course of one month, at which point patient is eating solid food. One month after initiating treatment, tests confirm the presence of endometrial cancer. By six weeks following treatment, patient shows no signs of abdominal swelling, and her blood work is returning to normal, patient resumes walking and normal menstruation. FIG. 3A is an ultrasound conducted four months after treatment showing a normal sized left ovary of 34×29 mm and an enlarged right ovary of 36×30 mm due to a solid tumor of 50×46 mm. A transvaginal ultrasound administered six months following the initiation of treatment with Formulation 1 shows a normal left ovary (34×29 mm) and a slightly enlarged right ovary (31×47.6) with a solid tumor contained within the ovary. Ten months after initiating treatment with Formulation 1 both ovaries are normal size with no tumor visible. FIG. 3B shows the right ovary now 29×30.1 mm in size. One year after initiating treatment with Formulation 1, patient leads a normal life while continuing to take Formulation 1 orally at a dose of 100 drops per day. Patient received no other treatment for her cancer.

EXAMPLE 23

Prostate Cancer

Male patient, age 64, suffered from frequent episodes of nighttime urination. Medical examination showed his PSA levels to be 33.49 ng/ml and rectal examination indicated a large prostate tumor with metastasis. Patient was very depressed. A second opinion which included a biopsy and echogram confirmed an aggressive carcinoma grade 9/10. An abdominal pelvic cat scan performed one week later showed calcification of the kidneys. Liver and spleen were normal size, uniform density and no focal alteration, incidentally a LOS (lesion of occupying space) of approximately 3 cm in diameter is shown at the right suprarenal level, represented by a low density nodular area. The left suprarenal area is normal. In the pelvis the prostate was observed to be 5 cm in diameter, a noticeable increase in size. Thickening of the back wall of the bladder was also observed and the prostate was exerting pressure on the bladder preventing expansion and increasing the frequency of urination. These findings suggested the presence of a neo proliferation. There are no lymphatic nodes increased in size in the pelvic compartments. Diverticulitis was also observed in the sigmoid colon. Following the CAT scan, patient initiated hormone treatment with Eleuxin tablets ever 8 hours and Zoladex one vial a month. The following week the patient underwent a transuretral resection of prostate.

Figure 4:
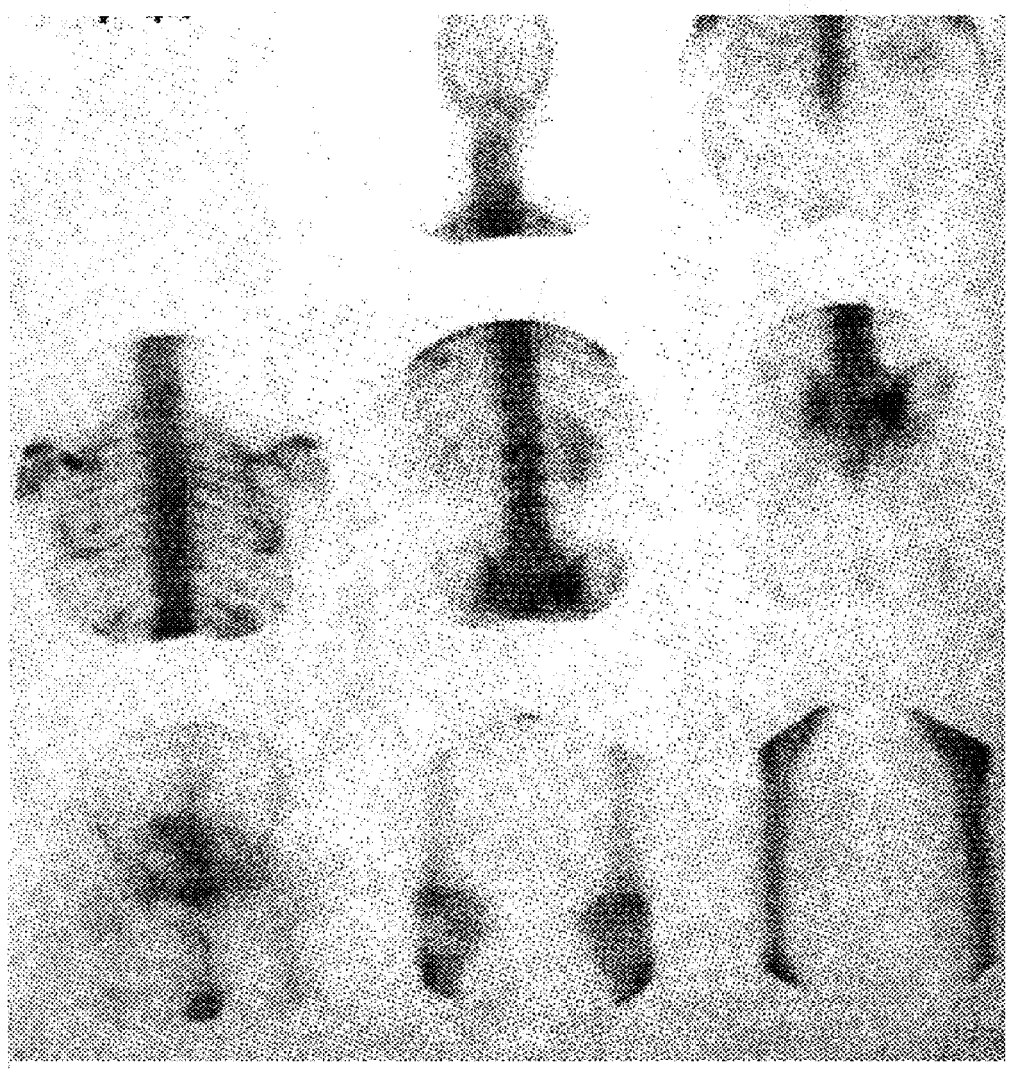
FIG. 4 is a bone scan of a prostate cancer patient showing metastatic bone cancer.

Three weeks after the initial diagnosis, the patient underwent a bone scan. The results of the bone scan are shown in FIG. 4. Metastasis to the bone, indicated by dark spots, are seen in the right scapula, left sacroilliac, L1 vertebra and in the ribs. At this time the patient initiated treatment with Formulation 1 at a dosage of 18 drops, 3 times a day, increasing 3 drops a day to reach 150 drops a day total by the end of 30 days. The patient continues to take 150 drops a day for two months and then reduced the dosage to 140 drops per day. The patient continues to take an average of 140 drops a day and continues to take prescribed doses of hormones.

Figure 5:
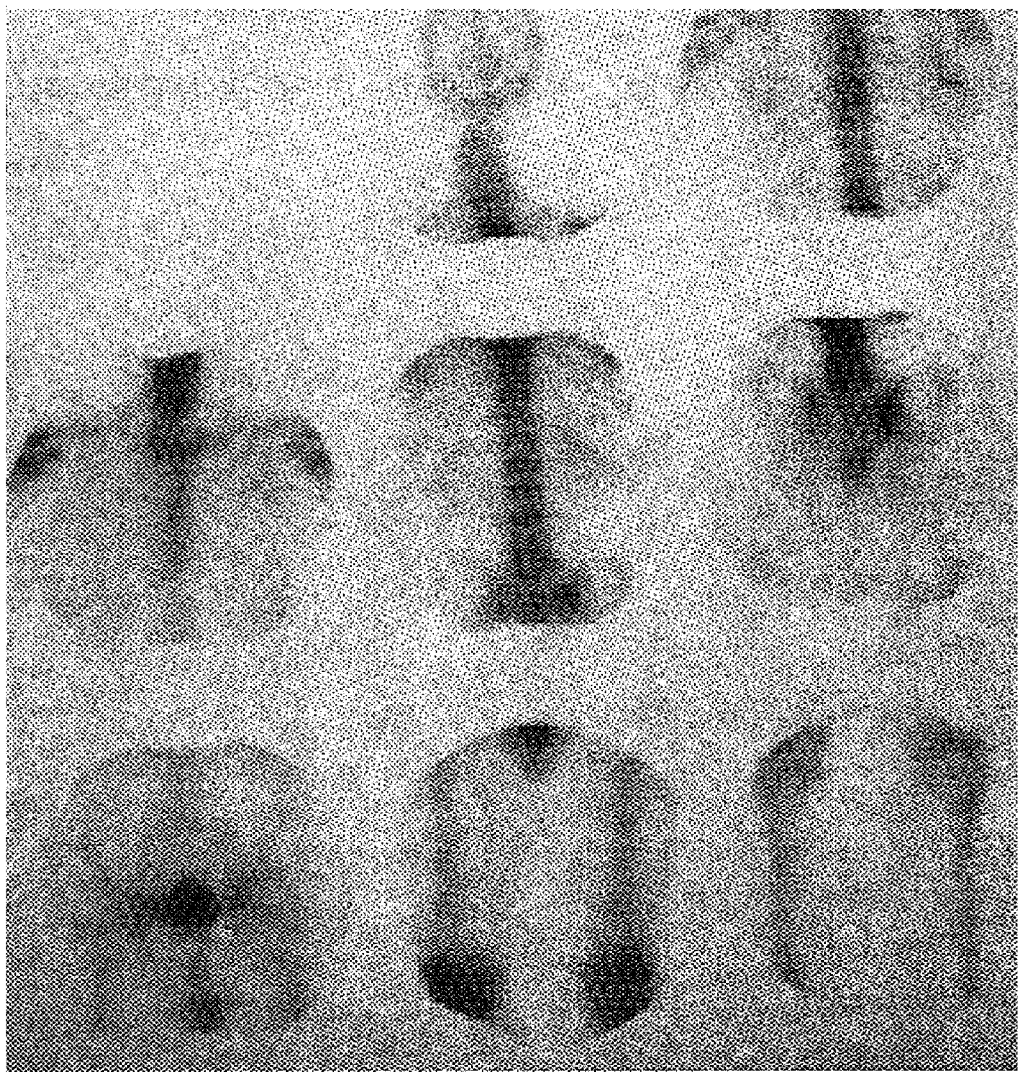
FIG. 5 is a bone scan of the same patient in FIG. 4 after treatment with Formulation 1 of the present invention.

Nine months post diagnosis of the tumor, the patient is normal with no abnormalities when palpated abdominally. A genital evaluation identified no pathological findings, and rectal exam identified a firm gland without well defined contours. Subject's PSA level at time of exam was 2.74 ng/ml. FIG. 5 is a bone scan taken 8 months after the original diagnosis and shows no sign of metastasis.

EXAMPLE 24

Adenocarcinoma of Right Parotid Gland

Female patient age 50 was diagnosed with an adenocarcinoma of the right parotid by examination confirmed as a 3.1 cm×1.7 cm×1.5 cm tumor through echogram and MRI. Surgery was performed approximately 7 months post diagnosis and a 3 cm tumor was extracted. The tumor returned at eight months with metastasis to the lymph nodes and the patient was treated with 25 sessions of radiotherapy over the following 8 months during which the tumor regressed. One year post diagnosis, a renal echogram was performed identifying a hydronephrosis and left kidney litaisis. Thirty four months following the original diagnosis, a Neoplastic Right Parotid Gland is again identified through MRI. Two months later the patient has an abdomen and pelvic ultrasound test, and the conclusions were:

1) Right Litiasis Renal Obstructive.
2) Renal Hydronephrosis IV/IV
3) Left Liatisasis non obstructive
4) Left Kidney of irregular shape, probably related to infectious process.

Patient decides not to undergo any further conventional therapy.

Approximately thirty-eight months following the initial diagnosis, the patient presents a painful, visible tumor of 7 cm of diameter with infiltration to the ear and pre auricular area. A Q-Tip cannot be introduced into the ear canal. The left side of the patients face suffered paralysis caused by the earlier radiation therapy and the patient had insomnia and cephalea. At this time the patient initiated oral treatment with Formulation 1 at an initial dose of 30 drops a day, increasing by 6 drops each day until reaching a maximum of 120 drops/day. Within one week the patient is taking 70 drops a day and is experiencing needle like sensations in the area of the tumor and that her head feels lighter. The attending physician observes the tumor to be visibly decreasing in size. One area of the tumor is squamous, when before is was plain. The following week the patient returned for observation complaining of dizziness and nausea. One month after initiating treatment the patient experienced headaches and lethargy but continued taking Formulation 1. Six weeks following treatment the patient returned for observation at which point the tumor is bleeding, but is noticeably softer, darker and smaller. By this time the dizziness and headaches have stopped and the patient feels well. The tumor continued to bleed and shrink until at two months after starting treatment a finger can be introduced in the ear.

By ten weeks the tumor shrunk further and shows necrosis until it broke inside the ear. The patient experienced bleeding through the mouth and ear. By twelve weeks following initialization of treatment, the tumor size is approximately 4 cm. Eighteen weeks after initiation of therapy with Formulation 1 the tumor has shrunk to 3 cm. The patient continues to take formulation 1.

EXAMPLE 25

Colon Cancer

Male patient, age 38, was diagnosed with adenocarcinoma of the rectum. Diagnosis followed patients suffering rectal bleeding, post-coital pain, loss of weight, changes in intestinal habits, and mid abdominal pain. 5 months after manifestation of symptoms, a Gastronterologist who identified a rectal mass and performed a colonoscopy and biopsy, with low anterior resection of the mass, evaluated subject. Subject pathology on the biopsy shows a T3-N1 Adenocarcinoma of the rectum with negative margins and one positive lymph node. Surgery was performed 7 months after initial diagnosis and the patient immediately underwent Radiotherapy (3960 cGy) for six months along with concurrent chemotherapy of 28 cycles of 5-FU and Leucovorin. The patient's CEA level (carcinoembriogenic antigen) was 0.7. at the time of initial diagnosis. Fourteen months following the initial diagnosis, another colonoscopy was performed revealing a small ulcerous lesion in the anastomosis line of the adrenal gland. The biopsy revealed small fragments of poorly differentiated adenocarcinoma. Because recurrent cancer was identified, the patient underwent a CT scan of the abdomen and pelvis and chest, along with x-ray and ultrasound. Tests failed to show any lung or liver metastasis. The patient could feel a nodular thickening of the rectum. At this time the patient was examined at M.D. Anderson Cancer Center and an additional 1.5 cm tumor in the lymph node identified.

The patient declined further radiotherapy, chemotherapy or further surgery. At seventeen months post diagnosis, the patient initiated oral treatment with Formulation 1 at an initial dose of 15 drops 3 times a day, increasing at a rate of 3 drops a day. The following week a subclavian catheter was installed and the patient began intravenous administration of Formulation 13 cc of 2 times a day (total 6 cc a day). While undergoing IV administration, patient continued to take Formulation 1 orally, up to 90 drops a day. During the second week of treatment with Formulation 1, the patient administered Formulation 1 rectally, diluted in 100 cc of saline for total of 15 continuous days using a rubber bulb. A total of 120 cc was administered via the subclavian catheter over 20 days at a dose of 6 cc a day. The patient continued taking Formulation 1 orally at about 90 drops a day after removal of the catheter.

Nineteen months post diagnosis, the patient reported that he could not feel the anal tumor; he felt in good physical condition, had resumed exercising and had regained his appetite.

20 months post diagnosis, a biopsy shows an adenocarcinoma moderately differentiated with ulceration and necropsies. A colonoscopy shows anastomosis approximately 5 cm from the anal exit, with 2 ulcerous areas. Multiple biopsies were taken and pictures were given to the patient. The attending physician was unable to find any tumor. There is no report of the lymph node discovered at MD Anderson. The only medication the patient has taken since his visit to MD Anderson is Formulation 1.

EXAMPLE 26

Extended Use Of Subclavial Ports

A 10 year old male patient suffering from cancer of the larynx had an external subclavian catheter installed. 3 cc of Formulation 1 diluted in physiological solution was administered twice a day for 95 days. At the time treatment with Formulation 1 was initiated, patient's esophagus was obstructed and patient could not eat. Patient was anemic with a hemoglobin level of 9. Following treatment the tumor shrank and the patient was able to eat normally. Further, the patient's hemoglobin level rose to 12. The catheter was in place for 95 days without any sign of infection.

EXAMPLE 27

Hypertension

A male patient aged 46 having hypertension since age 18 was treated with Formulation 1. Patient's normal blood pressure without any medication was 180/110 which caused patient severe headaches. Patient's blood pressure was stabilized at 150/90 through the administration of both Actbril and Atenolol twice daily for four years prior to beginning treatment with Formulation 1. Patient discontinued Actbril and Atenolol and immediately began taking 20 drops of Formulation 1 diluted in 250 ml of water twice a day. Patient's blood pressure has remained stable at 150/90 for more than 180 days following discontinuing Actbril and Atenolol. Prior to taking Formulation 1, patient experienced immediate elevation of blood pressure and headaches when discontinuing the actbril® and atenolol. Patient experienced no side effects of any kind from taking Formulation 1. Patient has only taken Formulation 1 to control his blood pressure for a period of six months.

EXAMPLE 28

Hypertension

An overweight 40 year old male patient with high blood pressure of 180/110 was administered Formulation 1 orally 40 drops per day. After 5 days, the patient's blood pressure stabilized at 140/90. Patient took no other medication.

EXAMPLE 29

USP51 Preservative Challenge Test

USP51 of the US Pharmacopoeia. It is a standard test that permits to determine if a medication requires of the presence of a preservative for its preservation, stability and packaging. The tests were carried out in the an independent testing facility located in Boston. Tests were performed at the following dilutions of Formulation 1:1:100, 1:250, 1:500 and 1:1000 in cuts of 7, 14 and 28 days for each dilution in the following micro-organisms: *S. Aureus, E. Coli, Ps. Aeruginosa, C. Albicans*, and *A. Niger*. Table 8 show similar results of the test at the different dilutions of Formulation 1, and its capacity to inhibit the growth of different micro organisms (i.e. Bacteria, Virus and Fungus).

TABLE 8

USP51 Preservative Challenge Test with Formulation 1
Dilutions: 1:100; 1:250; 1:500; 1:1000

| Test Organism | Initial Inoculum | Day 7 CFU/ml (% Red) | Day 14 CFU/ml (% Red) | Day 28 CFU/ml (% Red) |
|---|---|---|---|---|
| *S. Aureus* | $3.3 \times 10^5$ | <10 (>99.99%) | <10 (>99.99%) | <10 (>99.99%) |
| *E. Coli* | $3.9 \times 10^5$ | <10 (>99.99%) | <10 (>99.99%) | <10 (>99.99%) |
| *Ps. Aeruginosa* | $2.7 \times 10^5$ | <10 (>99.99%) | <10 (>99.99%) | <10 (>99.99%) |
| *C. Albicans* | $2.0 \times 10^5$ | <10 (>99.99%) | <10 (>99.99%) | <10 (>99.99%) |
| *A. Niger* | $3.1 \times 10^5$ | <10 (>99.99%) | <10 (>99.99%) | <10 (>99.99%) |

Conclusion: Formulation 1 meets the requirements of the USP51 for category 1A Products (Injectable Products).

The present invention has been set forth in the form of several preferred embodiments. It is nevertheless understood that modifications to the uses of the acid solutions disclosed herein may be made by those skilled in the art without departing from the scope and spirit of the present invention. Moreover, such modifications are considered to be within the purview of the appended claims.

I claim:

1. A method of reducing the risk of metastasis of a tumor comprising administering, to a patient in need thereof, a therapeutically effective amount of an aqueous pharmaceutical composition comprising a mixture of four strong acids and two weak acids wherein said composition comprises a mixture of sulfuric ($H_2SO_4$), hydrochloric (HCl), phosphoric ($H_3PO_4$) and oxalic ($H_2C_2O_4$) acids-as said strong acids- and citric ($H_8C_6O_7$) and hydrofluoric (HF) acids as said weak acids.

2. The method of claim 1 wherein the acids in the composition are present in the following concentrations by weight:

| | |
|---|---|
| HCl | 3–25% |
| $H_2C_2O_4$ | 0.1–10% |
| $H_3PO_4$ | 3–10% |
| HF | 1–30% |
| $H_2SO_4$ | 8–30% |
| $H_8C_6O_7$ | 0.1–10% . |

3. The method of claim 1 wherein the acids in the composition are present in the following concentrations by weight:

| | |
|---|---|
| HCl | 5–15% |
| $H_2C_2O_4$ | 0.15–2% |
| $H_3PO_4$ | 2–7% |
| HF | 2–7% |
| $H_2SO_4$ | 10–22% |
| $H_8C_3O_7$ | 0.15–2%. |

4. The method of claim 1 wherein the acids in the composition are present in the following approximate concentration by weight:

| | |
|---|---|
| HCl | 11% |
| $H_2C_2O_4$ | 0.3% |
| $H_3PO_4$ | 6% |
| $H_2SO_4$ | 16% |
| HF | 5% |
| $H_8C_6O_7$ | 0.3%. |

5. The method of claim 1 wherein the composition is administered through a method selected from the group consisting of: orally, intravenously, intramuscularly, intraperitoneally sub-cutaneously, rectally, intra-urethrally, topically intravesically, intravaginally, and combinations thereof.

6. The method of claim 5 wherein the composition is administered orally.

7. The method of claim 6 wherein the, patient is premedicated with a pharmaceutical product to protect against secretion of excess acid said product being selected from the group consisting of: $H_2$ blockers, digestive tract anti-inflammatories, antiemetics, and combinations thereof.

8. The method of claim 5 wherein the composition is administered intravenously.

9. The method of claim 8 wherein the acid composition is infused over a period of 1–8 hours.

10. The method of claim 5 wherein the composition is administered intramuscularly.

11. The method of claim 5 wherein the composition is administered subcutaneously.

12. The method of claim 5 wherein the composition is administered intraperitoneal.

13. The method of claim 5 wherein the composition is administered intraurethrally.

14. The method of claim 5 wherein the composition is administered rectally.

15. The method of claim 5 wherein the composition is administered topically.

16. The method of claim 5 wherein the composition is administered intravesical.

17. The method of claim 5 wherein the composition is administered intravaginal.

18. The method of claim 5 wherein the composition is administered via a central venous access.

19. The method of claim 5 wherein the composition is administered by means of a subclavian catheter.

20. The method of claim 5 wherein the composition is administered via a peripheral catheter.

21. The method of claim 1 wherein the patient is administered from 5 to 1000 drops of the composition per day.

22. The method of claim 1 wherein the patient is administered from 50 to 500 drops of the composition per day.

23. The method of claim 1 wherein the patient is administered from 100 to 250 drops of the composition per day.

24. The method of claim 1 wherein the daily dosage is divided into portions administered multiple times daily.

25. The method of claim 1 wherein the composition is administered in doses ranging from 20 to 80 drops during a time period ranging from 1 to 10 hours per day.

26. The method of claim 1 wherein the composition is administered in doses ranging from 20 to 80 drops from between 2 to 5 times per day.

27. The method of claim 1 wherein the composition is diluted prior to administration.

28. The method of claim 1 wherein the composition is diluted in a dietetically safe liquid, which liquid is not a dairy product and does not curdle in acid or a citrus juice.

29. The method of claim 1 wherein the composition is diluted at a ratio of from 20–80 drops of acid solution per 50–500 ml of liquid.

30. The method of claim 1 wherein the composition is diluted in ratio of 20–80 drops of acid solution per 100–300 ml of liquid.

31. The method of claim 1 wherein the composition is diluted in ratio of 20–80 drops of acid solution per 250 ml of liquid.

32. The method of claim 1 wherein the acid composition is diluted in a ratio of 1–8 ml of acid solution per 100–1000 ml of liquid of any solution acceptable for intravenous administration.

33. The method of claim 1 wherein the acid composition is diluted in a ratio of 1–8 ml of acid solution per 100–1000 ml of an intravenous acceptable solution selected from the group consisting of: saline, glucose, dextrose, and combinations thereof.

34. The method of claim 1 wherein the patient is dosed at least once per day, every other day for at least 1 week.

35. The method of claim 1 wherein the patient is dosed at least once per day, daily, for at least 1 week.

36. A method of inhibiting metastasis of a tumor comprising administering, to a patient in need thereof, a therapeutically effective amount of an aqueous pharmaceutical composition comprising a mixture of four strong acids and two weak acids wherein said composition comprises a mixture of sulfuric ($H_2SO_4$), hydrochloric (HCl), phosphoric ($H_3PO_4$) and oxalic ($H_2C_2O_4$) acids as said strong acids-and-citric ($H_8C_6O_7$) and hydrofluoric (HF) acids as said weak acids.

37. The method of claim 36 wherein the acids in the composition are present in the following concentrations by weight:

| | |
|---|---|
| HCl | 3–25% |
| $H_2CO_4$ | 0.1–10% |
| $H_3PO_4$ | 3–10% |
| HF | 1–30% |
| $H_2SO_4$ | 8–30% |
| $H_8C_6O_7$ | 0.1–10%. |

38. The method of claim 36 wherein the acids in the composition are present in the following concentrations by weight:

| | |
|---|---|
| HCl | 5–15% |
| $H_2C_2O_4$ | 0.15–2% |
| $H_3PO_4$ | 2–7% |
| HF | 2–7% |
| $H_2SO_4$ | 10–22% |
| $H_8C_6O_7$ | 0.15–2%. |

39. The method of claim 36 wherein the acids in the composition are present in the following approximate concentration by weight:

| | |
|---|---|
| HCl | 11% |
| $H_2C_2O_4$ | 0.3% |
| $H_3PO_4$ | 6% |
| $H_2SO_4$ | 16% |
| HF | 5% |
| $H_8C_6O_7$ | 0.3%. |

40. The method of claim 36 wherein the composition is administered through a method selected from the group consisting of: orally, intravenously, intramuscularly, intraperitoneally sub-cutaneously, rectally, intraurethrally, topically, intravesically, intravaginally, and combinations thereof.

41. The method of claim 40 wherein the composition is administered orally.

42. The method of claim 41 wherein the patient is premedicated with a pharmaceutical product to protect against secretion of excess acid said product being selected from the group consisting of: $H_2$ blockers, digestive tract anti-inflammatories, antiemetics, and combinations thereof.

43. The method of claim 40 wherein the composition is administered intravenously.

44. The method of claim 43 wherein the acid composition is infused over a period of 1–8 hours.

45. The method of claim 40 wherein the composition is administered intramuscularly.

46. The method of claim 40 wherein the composition is administered subcutaneously.

47. The method of claim 40 wherein the composition is administered intraperitoneal.

48. The method of claim 40 wherein the composition is administered intraurethrally.

49. The method of claim 40 wherein the composition is administered rectally.

50. The method of claim 40 wherein the composition is administered topically.

51. The method of claim 40 wherein the composition is administered intravesical.

52. The method of claim 40 wherein the composition is administered intravaginal.

53. The method of claim 40 wherein the composition is administered via a central venous access.

54. The method of claim 40 wherein the composition is administered by means of a subclavian catheter.

55. The method of claim 40 wherein the composition is administered via a peripheral catheter.

56. The method of claim 36 wherein the patient is administered from 5 to 1000 drops of the composition per day.

57. The method of claim 36 wherein the patient is administered from 50 to 500 drops of the composition per day.

58. The method of claim 36 wherein the patient is administered from 100 to 250 drops of the composition per day.

59. The method of claim 36 wherein the daily dosage is divided into portions administered multiple times daily.

60. The method of claim 36 wherein the composition is administered in doses ranging from 20 to 80 drops during a time period ranging from 1 to 10 hours per day.

61. The method of claim 36 wherein the composition is administered in doses ranging from 20 to 80 drops from between 2 to 5 times per day.

62. The method of claim 36 wherein the composition is diluted prior to administration.

63. The method of claim 36 wherein the composition is diluted in a dietetically safe liquid, which liquid is not a dairy product and does not curdle in acid or a citrus juice.

64. The method of claim 36 wherein the composition is diluted at a ratio of from 20–80 drops of acid solution per 50–500 ml of liquid.

65. The method of claim 36 wherein the composition is diluted in ratio of 20–80 drops of acid solution per 100–300 ml of liquid.

66. The method of claim 36 wherein the composition is diluted in ratio of 20–80 drops of acid solution per 250 ml of liquid.

67. The method of claim 36 wherein the acid composition is diluted in a ratio of 1–8 ml of acid solution per 100–1000 ml of liquid of any solution acceptable for intravenous administration.

68. The method of claim 36 wherein the acid composition is diluted in a ratio of 1–8 ml of acid solution per 100–1000 ml of an intravenous acceptable solution selected from the group consisting of: saline, glucose, dextrose, and combinations thereof.

69. The method of claim 36 wherein the patient is dosed at least once per day, every other day for at least 1 week.

70. The method of claim 36 wherein the patient is dosed at least once per day, daily, for at least 1 week.

* * * * *